United States Patent [19]

Lagow et al.

[11] 3,992,424

[45] Nov. 16, 1976

[54] TRIFLUOROMETHYL-SUBSTITUTED COMPOUNDS

[75] Inventors: Richard J. Lagow, Manchester; Lois L. Gerchman, Stoneham, both of Mass.; Robert A. Jacob, Grand Forks, N. Dak.

[73] Assignee: Massachusetts Institute of Technology, Cambridge, Mass.

[22] Filed: Oct. 1, 1975

[21] Appl. No.: 618,525

Related U.S. Application Data

[62] Division of Ser. No. 444,465, Feb. 21, 1974.

[52] U.S. Cl. .................... 260/429.1; 260/429 R; 260/429.2; 260/429.7; 260/448 A
[51] Int. Cl.$^2$ .................. C07F 5/00; C07F 5/06
[58] Field of Search ........ 260/429 R, 429.1, 448 A, 260/429.7

[56] References Cited
UNITED STATES PATENTS

3,794,671    2/1974    Wilkinson .................. 260/429 R

OTHER PUBLICATIONS

Jacob et al., Chem. Soc. Journal, Chemical Communications, 1973, No. 4, pp. 104–105.
Lagow et al., J. Am. Chem. Soc., vol. 97, pp. 518–522 (1975).

*Primary Examiner*—Leland A. Sebastian
*Attorney, Agent, or Firm*—Arthur A. Smith, Jr.; Robert Shaw; Paul J. Cook

[57] ABSTRACT

Trifluoromethyl-substituted compounds, are formed in a corona discharge or glow discharge plasma of trifluoromethyl radicals from an organic trifluoromethyl source. A substrate possessing easily replaceable ligands such as halogen or carbonyl, is initially contacted either in the plasma and within a short distance from a downstream visible edge of the plasma or outside of the visible portion of the plasma and within a short distance from the downstream visible edge, to effect a substitution of the halogen or carbonyl ligand on the substrate with a trifluoromethyl radical without substantial decomposition of the substrate.

9 Claims, 1 Drawing Figure

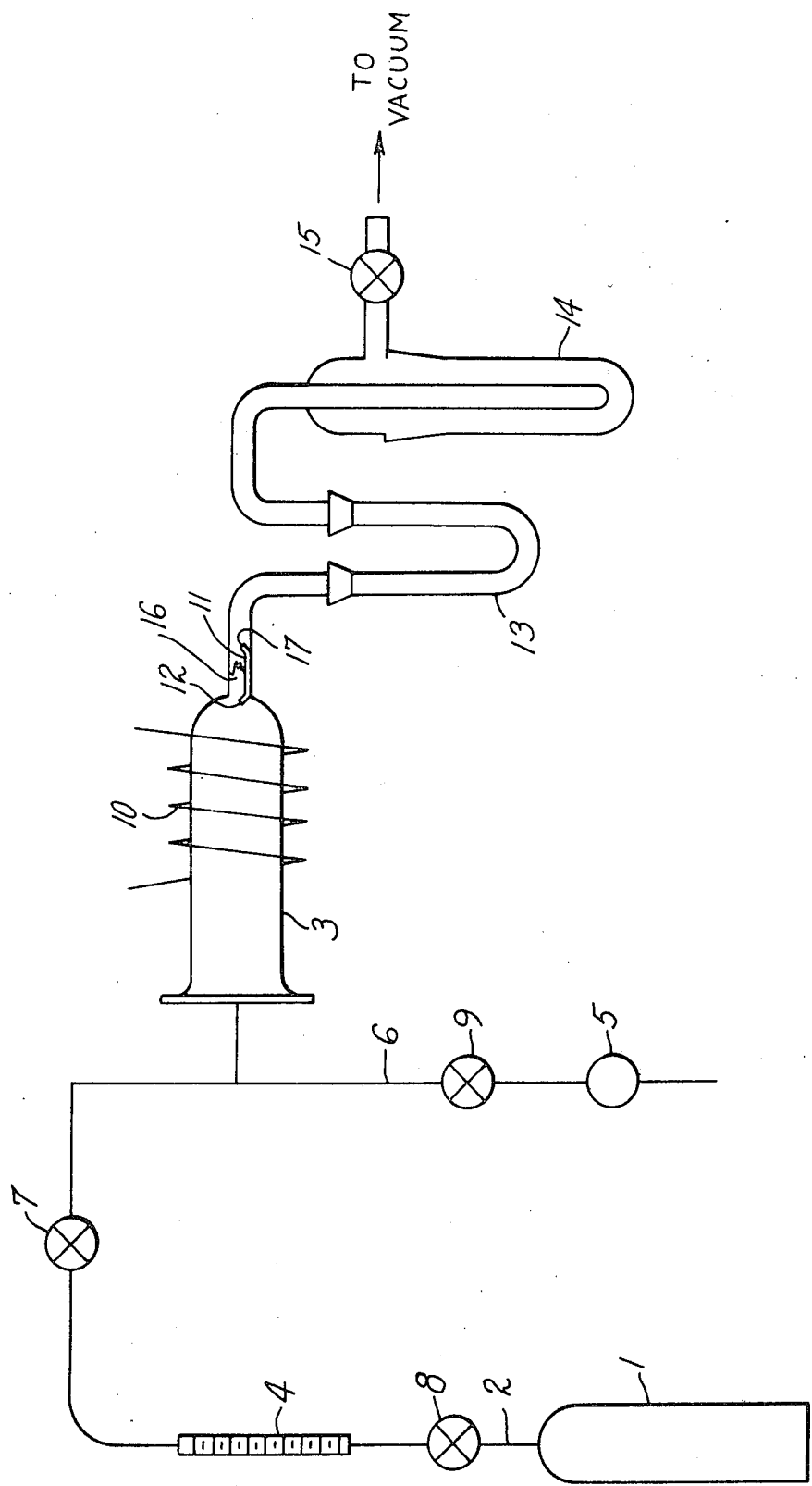

TRIFLUOROMETHYL-SUBSTITUTED COMPOUNDS

The Government has rights in this invention pursuant to Grant No. NSF-75-30A-GP-30484 and IPA-0010 awarded by the National Science Foundation.

This is a division of application Ser. No. 444,465, filed Feb. 21, 1974.

BACKGROUND OF THE INVENTION

The present invention relates to a process for forming trifluoromethyl-substituted compounds employing a low energy plasma as an energy source and to the trifluoromethyl-substituted compounds produced thereby.

Prior to the present invention, trifluoromethyl radicals have been formed by passing a trifluoromethyl-substituted organic compound as feed through a plasma formed by radio frequency discharges, which radicals are contacted with a substrate to form trifluoromethyl-substituted compounds. This low power glow discharge or corona discharge provides a convenient synthetic route to a large number of novel inorganic compounds by forming from the feed highly reactive radicals and atoms in excited electronic states at gas temperatures of from about 30° to 100° C. These reactive species are normally found only at high temperatures and are characteristic of temperatures in excess of 1000° C. Thus, the "cold" plasmas, i.e. glow discharge or corona discharge, offers the advantage of high energy species at temperatures where chemical reactions can occur without degradation of the substrate or products.

The generation of trifluoromethyl radicals is a particularly interesting case. For example, the carbon-carbon bond in hexafluoroethane is anomalously weak due to the strong electron withdrawing effect of the six fluorine atoms. The best estimate of the actual bond strength at present is 68–82 Kcal/mole as compared to 86–88 Kcal/mole for the average carbon-carbon bond. The carbon-fluorine bond energies in hexafluoroethane are 114–119 Kcal/mole and thus one has a difference in bond energy of 32–51 Kcal/mole between the two types of bonds in the compound. When hexafluoroethane is introduced into the glow discharge, the initially available electrons in the gas gain energy from the applied radio frequency field. When the discharge is initiated, more electrons become available through partial ionization of radicals. The electron energies approximate a Maxwellian distribution and it is only the electrons in the high energy end of this distribution which are responsible for fragmentation of the hexafluoroethane upon collision. There are several available mechanisms by which fragmentation may occur. The two processes of lowest energy are the breaking of carbon-carbon and carbon-fluorine bonds, and these appear to be the most prominent processes in the low energy glow discharge region.

The most commonly employed source of trifluoromethyl radicals is the compound, hexaflouroethane, although other sources have been employed. At one time, it was thought necessary to trap the trifluoromethyl radicals in an inert solidified matrix at low temperatures prior to reaction with a substrate as exemplified by U.S. Pat. Nos. 3,196,115 and 3,240,691. Unfortunately, this process has substantial disadvantages which have seriously limited its use. While the frozen free radicals can be evolved subsequently from the solid matrix by heating the matrix, the radicals so evolved have very little energy so that they are reactive only with very limited substrates such as fluorine, chlorine, or bromine. Even with these substrates, the radicals are more reactive with themselves than with the substrate.

Alternatively it has been proposed to pass a trifluoromethyl radical source and the substrate simultaneously through an electrically induced plasma as shown in German DOS No. 2,060,351. As shown in the German publication, the substrate constitutes iodine which is decomposed in the plasma to form iodo radicals which combine with the trifluoromethyl radicals formed from hexafluoroethane. Unfortunately, such a process is not suitable if it causes the substrate to decompose into radicals which themselves may be decomposed further or which will react preferentially with each other rather than with the trifluoromethyl radicals. For example, if a metal halide substrate were passed through the entire plasma admixed with the trifluoromethyl radicals, a substantial portion of the metal would plate out on the inner reactor wall thereby substantially reducing the yield of a trifluoromethyl-substituted metal compound. Also, when organic substrates are employed as the reactant, the organo radical formed in the plasma will itself become decomposed to form, among other by-products, coke. This, of course, is undesirable since the product yield will be reduced substantially.

SUMMARY OF THE INVENTION

The present invention is based upon the discovery that trifluoromethyl-substituted compounds can be produced by reacting a trifluoromethyl radical formed in a low energy plasma, that is, a glow discharge or a corona discharge, with an organic or inorganic substrate containing a weakly bonded ligand(s) such as halide or carbonyl, wherein contact of the two reactants is conducted either downstream and adjacent to the visible plasma or within only a small portion of the visible plasma to substantially reduce or eliminate free-radical formation from the substrate. The reaction is conducted under conditions to effect substitution of the halogen or carbonyl ligand with an energized trifluoromethyl radical.

DESCRIPTION OF SPECIFIC EMBODIMENTS

For convenience, this invention will be described specifically herein with reference to hexafluoroethane as the trifluoromethyl radical source although it is to be understood that alternative trifluoromethyl radical sources can be used and with reference to halogenated substrates. The hexafluoroethane is passed through a low energy plasma, that is, a glow discharge or corona discharge maintained at a sufficiently high energy to break the carbon-to-carbon bond which has an energy in the order of about 60 or 70 kilocalories. However, the plasma is not maintained at such a high energy level as to cause excessive breaking of the carbon to fluorine bonds which have a bond strength in the order of 116 to 120 kilocalories. It has been found that by operating within this energy level, trifluoromethyl radicals are produced which are sufficiently excited to enter into a substitution reaction with the halogen-substituted substrate. The plasma can be produced by any conventionally available means such as a radio frequency discharge, a microwave discharge or with electrodes. Suitable plasmas can be formed with a radio frequency discharge operated between about 350 kilohertz to 600 megahertz and about 10 to 100 watts or with a microwave discharge operated between about 800 to 3000 megahertz and about 10 to 300 watts. These wattage considerations are based upon a three inch diameter reactor and may be increased for a larger reactor.

The halogen-substituted substrate is contacted with the trifluoromethyl radicals when the trifluoromethyl radicals are sufficiently excited to replace the halogen(s) of the substrate. The products are prevented from being retained in the plasma for such a time as to cause substantial decomposition thereof by virtue of the energy of the plasma. The haolgen substrate is contacted initially with the trifluoromethyl radicals at a position relative to the plasma so that the desired substitution reaction occurs without causing substantial decomposition of the substrate and without excessive recombination of the trifluoromethyl radicals. For example in a 3 inch diameter reactor at 1 mm Hg pressure, the halogen-substituted substrate is introduced into the downstream end of the visible plasma within up to about 3 inches of the end of the visible portion of the plasma, or outside of the visible plasma but within up to about 3 inches of the downstream end of the visible plasma. In this portion of the plasma, the halogenated reactant does not decompose to such an undesirable degree as to provide substantial reduction in the yield of the desired product. On the other hand, when a metal halide reactant is introduced into the plasma at a point where undesirable residence times thereof in the plasma result, the metal halide will become dissociated and the metal ions will plate out on the surface of the reactor walls. On the other hand, when the metal halide reactant is an organo halide, the organo radical formed by the dissociation will itself become further decomposed to form carbon atoms having a low degree of hydrogen substitution such as coke. In this manner, the reaction can be effected as a substitution reaction rather than as a reaction involving the formation of free radicals which then combine to form the desired product. By operating in this manner, substantial advantages are obtained, particularly due to the high yields that can be obtained.

This invention is particularly useful for reacting trifluoromethyl radicals with metal halides to form trifluoromethyl-substituted metal compounds having varying degrees of trifluoro-methyl substitution. This invention also provides novel metal trifluoromethyl compounds including compounds derived from metals of the lathanide and actinide series such as uranium and plutonium and compounds derived from transition metals such as mercury and tungsten, as well as main group metals such as germanium and tin. The metal compounds of this invention are useful as polymerization catalysts for olefins such as ethylene and are useful as dihalocarbene donors.

The process of the present invention is exemplified by the following equation:

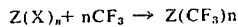

wherein Z can be any acyclic or cyclic radical including alkyl such as methyl, ethyl, propyl, butyl or the like, alkenyl such as vinyl, propenyl or the like, alkynyl such as acetylenyl or the like, cycloalkyl such as cyclobutyl, cyclohexyl, cycloheptyl or the like, aromatic such as phenyl, tolyl, xylyl or the like, condensed ring aromatic such as anthracenyl, fluorenyl or the like as well as a polymeric hydrocarbon or any metal such as mercury, tin, tungsten, urnanium, plutonium, sodium, cobalt, molybdenum or the like or an amphoteric element such as silicon or tellurium; X is a halogen including fluorine, bromine, chlorine, and iodine, or carbonyl, n is a whole number corresponding to the degree of halogen or carbonyl substitution. Preferably, X is iodine or bromine. Reaction is effected by contacting the trifluoromethyl radical with a liquid, solid or vapor substrate in a dry non-oxidizing atmosphere. Reaction can be effected either in a vacuum of less than about 1 mm Hg, in an inert atmosphere such as helium, argon, neon, krypton, xenon or the like or in an atmosphere of the trifluoromethyl radicals at pressures up to about 1 atmosphere so long as the temperature in the reactor is maintained below the product decomposition temperature. The ratio of reactants is at least stochiometric, based upon the above equation, and preferably with an excess of the trifluoromethyl radicals of at least 2:1, preferably 20:1 above stochiometric in order to effect as complete substitution as possible of the trifluoromethyl radicals for the ligard atoms on the substrate. The products are isolated for example by trap to trap distillation, gas chromatography or separation in a low temperature still.

The degree of trifluoromethyl substitution is controlled primarily by the mole ratio of halogenated substrate to trifluoromethyl radical and by the energy level to which the reactants are raised prior to and during reaction. Energy sources supplementing the plasma also can be employed to activate the trifluoromethyl radicals to high energy. Suitable supplemental methods include ultraviolet radiation, and conventional radiation sources such as x-rays, gamma rays or high energy electrons.

It is preferred to conduct the reaction in a vacuum since the presence of an inert gas in the reaction chamber reduces the mean free path of the reactants thereby requiring higher vapor temperatures of the reactants to effect a given reaction rate.

While the invention has been described above with reference to a one step contact of the halogenated reactants with trifluoromethyl radicals, it is to be understood that the process of this invention can be conducted in a multi-step procedure wherein the partially substituted halogenated reactant is reacted in a first step to effect less than complete trifluoromethyl substitution and thereafter the product can be reacted with additional trifluoromethyl radicals.

By employing the process of this invention, novel pertrifluoromethyl-substituted metal compounds are produced, particularly per(trifluoromethyl) metals of the lanthanide and actinide series. Exemplary novel compounds include bis(trifluoromethyl) tellurium, tetrakis(trifluoromethyl) tin, tetrakis(trifluoromethyl) platinum, tetrakis(trifluoromethyl) uranium, hexakis(trifluoromethyl) uranium, per(trifluoromethyl) plutonium and the like. The formation of these metal trifluoromethyl compounds is particularly useful when it is desired to separate isotopes of the particular metals involved by photodissociation, either by vibrational decomposition with an infrared laser or decomposition by overexcitation of isotopes electronically with an ultraviolet laser or by conventional diffusion techniques. Most of the metal trifluoromethyl compounds produced in accordance with this process are normally vaporous products whose isotopes can be separated by these known techniques, most particularly U-235 from U-238.

This invention will be more fully described with reference to the FIGURE which is a schematic diagram of apparatus useful for practicing the invention.

As shown in the FIGURE, a container for hexafluoroethane is provided with a conduit to deliver hexafluoroethane to a quartz reactor 3. A flowmeter 4 is provided for measuring gas flow rates and a vacuum gauge 5 is provided in conduit 6 to monitor the pressure within the reactor system. Valves 7, 8 and 9 are provided in conduits 2 and 6 to regulate the flow rate of hexafluoroethane to reactor 3. A typical quartz reactor is 30 cm long and has an outside diameter of 75mm. Prior to use, the reactor 10 is evacuated by opening valve 15 to a vacuum source (not shown). A suitable helical coil 10 consists of seven turns of a 3/16 inch copper tubing forming an 11 cm outside diameter helix which is connected to a suitable radio frequency oscillator (not shown). A suitable radio frequency oscillator is operated at a frequency of from about 100 Kilohertz to 3,000 Megahertz preferably from 900 Kilohertz to 2,000 Megahertz. A solid halogenated substrate to be reacted with the trifluoromethyl radicals is placed in a Vycor container 11 with the upstream tip 12 thereof located in the visible plasma and about 1 inch from the edge 16 of the visible plasma. The downstream tip 17 is located outside the visible plasma and about 1 inch downstream for the edge 16. The traps 13 and 14 are cooled to suitable temperatures in order to collect all products from the reaction. When employing a vaporous substrate or an easily vaporizable liquid substrate, it can be conveniently introduced into the reactor apparatus by employing a conduit attached to reactor 10 in the area occupied by container 11.

The following examples illustrate the present invention and are not intended to limit the same.

EXAMPLE I

Employing a reactor system of the general arrangement shown in the FIGURE, tetrakis(trifluoromethyl) tin was prepared as follows: hexafluoroethane was passed into a quartz reactor having a 3 inch outside diameter which tapered sharply to one inch outside diameter. Radio frequency coils were positioned around the smaller end of the quartz reactor so that the tail of the plasma produced, which was blue to violet, extended out of the larger chamber and about half the length of a Vycor conatiner positioned within the one inch outside diameter portion of the reactor. After evacuation of the reactor, the hexafluoroethane pressure was adjusted to 0.5–1mm pressure with a flow rate of 15 cm$^3$ per minute. The Vycor sample vessel contained tin(IV) iodide.

The volatile $Sn(CF_3)_4$ was recovered in two traps downstream from the reactor. A trap at −78° C contained a small amount of nearly pure $Sn(CF_3)_4$; and most of the $Sn(CF_3)_4$, a volatile colourless solid, was recovered in a subsequent −196° C trap along with fluorocarbons. The products were extracted with benzene and $Sn(CF_3)_4$ was separated from the extract by g.l.c. The yield was over 90% based on $SnI_4$ and a typical 4 h run yielded 19 mg $Sn(CF_3)_4$ (0.048 mmol). The product had a correct C and F analysis. The 56.47 MHz $^{19}F$ n.m.r. spectrum of neat $Sn(CF_3)_4$ consisted of a singlet at −21 ± 1 p.p.m. from external trifluoromethylbenzene, and symmetrical double satellites due to tin isotope coupling [I = ½, $^{117}Sn$, $^{119}Sn$; J ($^{119}Sn$—F) 9.4± 0.1, J ($^{117}Sn$—F) 8.9 ± 0.1 p.p.m.]. The chemical shift of $Sn(CF_3)_4$ in benzene is −18 ± 1 p.p.m. The mass spectrum consisted of $Sn(CF_3)n$ ($n$ = 1,2,3) species and fluorocarbon fragments and an isotopically correct pattern around 327 for $^{120}Sn(CF_3)_3$ was of highest molecular weight. A peak at 377 (P − 19) was observed of insufficient intensity to determine the isotope distribution. The i.r. spectrum contained carbon-fluorine stretches at 1150 and 1238 cm$^{-1}$ and a band at 744 cm$^{-1}$ which is probably a $CF_3$ deformation.

If the $SnI_4$ were positioned in the reactor to promote partial reaction, the new compounds $Sn(CF_3)_3I$ [−19.8 p.p.m., J ($^{119}Sn$—F) 10,3 ± 0.1 p.p.m.]and $Sn(CF_3)_2I_2$ [−16.4 p.p.m., J ($^{119}Sn$—F) 10:9 ± 0.1, J ($^{117}Sn$—F) 10.4 ± 0.1 p.p.m.] are produced. The use of other tin halides produces other new $Sn(CF_3)n$ $X_{4-n}$ species but lower yields of $Sn(CF_3)_4$ are observed with about the same total yield.

EXAMPLE II

Employing the apparatus shown in the figure, trifluoromethyl-substituted mercury compounds were produced as follows: The Vycor boat was filled with enough of one of the finely powdered mercury halides set forth below to cover the bottom to a depth of at least 3mm, then weighed. A liquid nitrogen trap was placed on the trap immediately adjacent the vacuum pump, and the system was pumped down to 0.1 Torr or less. A dry ice-acetone bath was then placed on the U-trap. The flow rate of hexafluoroethane was adjusted to 15 cc/min which corresponds to a system pressure of 0.5 Torr as measured with the thermocouple vacuum gauge. The 15 cc/min flow rate was found to be optimum. Small deviations from this flow rate are inconsequential, but best results were obtained with a flow rate in the range of 11–17 cc/min.

Blue plasma discharge then was initiated by applying power to the coil. After a typical run of 5 hours, the U-trap was weighed and the contents were extracted with benzene. Fluorine$^{19}$ nmr spectra then were taken from the raw extracts as well as the purified compounds. The extracts contained the soluble bis(trifluoromethyl)mercury, the trifluoromethylmercuric halides, and where appropriate, iodine. The volatile benzene and iodine were later separated from the mercurials on a vacuum line. The crude bis(trifluoromethylmercury was then easily purified by high vacuum sublimation at 35° C. The respective trifluoromethylmercuric halide was subsequently recovered by vacuum sublimation at 70–100° C.

Bis(trifluoromethyl)mercury was obtained in all of the reactions discussed below but is produced in highest yield from the reaction of $CF_3$ with mercuric iodide according to the procedure outlined above. The amount obtained in a 5-hour run is in excess of 0.5 gram. Trifluoromethylmercuric iodide was obtained in low yield (0.02 g) from the reaction of $CF_3$ with mercuric iodide. Trifluoromethylmercuric bromide was obtained from the reaction of $CF_3$ with mercuric bromide (0.3 g). Trifluoromethylmercuric chloride was obtained from the reaction of $CF_3$ with mercuric chloride (0.4 g).

The reaction of mercuric iodide, mercuric bromide, and mercuric chloride with plasma-generated $CF_3$ radicals produces a mixture of bistrifluoromethylmercury and the corresponding trifluoromethylmercuric halide. With mercuric iodide very little trifluoromethylmercuric iodide is collected. The relative and actual amounts of product produced in each reaction are tabulated in Table I. The amounts reported in Table I are for average five-hour runs.

The volatile products were analyzed in a mass spectrometer. With mercuric iodide as substrate, iodine was found in all experiments run in the 20-watt power region for the radio frequency coil and a trace of $CF_3I$ was observed in only one run.

The unreacted hexafluoroethane and recombination products from the liquid nitrogen trap were analyzed mass spectrometrically. While $C_2F_6$ was the major component, fluorocarbons containing up to six carbon atoms were identified.

TABLE I

Yields of Perfluoroorganomercurials

| Compound | Mole Ratio $\frac{Hg(CF_3)_2}{HgCF_3X}$ | Amount Recovered (g) $Hg(CF_3)_2 + HgCF_3X$ |
|---|---|---|
| $CF_3HgI$ | 24 | 0.69 |
| $CF_3HgBr$ | 0.85 | 0.55 |
| $CF_3HgCl$ | 0.11 | 0.44 |

EXAMPLE III FIGURE

Employing the apparatus described above, tetrakis(trifluoromethyl)germanium was prepared as follows: 5 grams of $GeI_4$ or $GeBr_4$ were placed in the Vycor container and the reactor was evacuated to 0.1 mm pressure. The Vycor container was positioned as shown in the FIGURE. The hexafluoroethane was admitted to the reactor at a flow rate of 15 cc/min and the discharge was initiated with a 10 megahertz, 20 watt radio frequency generator. After 8 hours the product was removed along with the fluorocarbons from a $-196°$ C trap downstream from the plasma reactor. The material, a colorless solid, was separated from fluorocarbon by trap to trap distillation and further purified on a liquid nitrogen-cooled gas chromatographic column. The yield was 80% based on the germanium halide. The compound was characterized by a mass spectrum which contained a parent $-$ 19 and a parent $-$ $CF_3$ peak. the $F^{19}$ N.M.R. of $Ge(CF_3)_4$ consists of a singlet at $-25.2$ ppm from extermal trifluoroacetic acid.

EXAMPLE IV

Perfluoroneopentane is prepared from $CI_4$ employing the apparatus described above. Five grams of carbon tetraiodide were placed in the Vycor container and the reactor was evacuated to 0.1 mm pressure. The Vycor container is located as in the position shown in the FIGURE. Hexafluoroethane was admitted to the reactor at a flow rate of 15 cc/min to maintain a 0.5 to 1 mm pressure during constant pumping. The discharge was initiated at 10 megahertz and 20 watts using a radio frequency generator. After eight hours the products were removed along with fluorocarbons from a $-196°$ C trap downstream from the reactor. The products were separated from fluorocarbons by trap to trap distillation and purified using liquid nitrogen-cooled columns of a gas chromatograph. A 55% yield of the white solid $CI(CF_3)_3$ was obtained, which had a $F^{19}$ N.M.R. singlet $-13.3$ ppm from external trifluoroacetic acid. The mass spectrum contained a parent at 346 and a P-19 peak at 327. The infrared spectrum contained peaks at (1270) (960) and (725) $cm^{-1}$. The elemental analysis was in agreement with the calculated values.

The perfluoroneopentane $C(CF_3)_4$ was obtained in 25% yield and is a white solid melting at 72.5° to 73° C. The mass spectrum of the compound contains a P-19 at 269 while the $F^{19}$ N.M.R. consists of a singlet at $-13.92$ ppm from external trifluoroacetic acid. The infrared spectrum contains peaks at (9.80) (720) and 1190 $cm^{-1}$.

EXAMPLE V

Hexakis(trifluoromethyl)tungsten is prepared from $WBr_6$ employing the apparatus described above with the Vycor container being located in the position shown in the FIGURE. Five grams of $WBr_6$ is placed in the Vycor container and the reaction chamber is evacuated to $10^{-3}$ torr. Hexafluoroethane then is admitted to the reactor at a flow rate of 15 cc/min to maintain a 0.5 to 1 mm pressure during pumping. The plasma is initiated at 10 megahertz and 20 watts with a radio frequency generator. After 10 hours the product is removed along with fluorocarbons from a $-196°$ C trap downstream from the plasma reactor. The product is separated from fluorocarbons by trap to trap distillation and purified by using a liquid nitrogen still technique. A white sublimable solid which slowly passes a $-95°$ C trap and which melts below room temperature was obtained. This compound $W(CF_3)_6$ exhibits a parent and a parent $-19$ peak in its mass spectrum. The $F^{19}$ N.M.R. spectrum occurs at $+25.7$ ppm from external trifluoroacetic acid and has a coupling constant $J183$ W - F of $21.8Hz$. When $WCl_6$ is substituted for $WBr_6$ in the process of this example, the same tungsten compound is obtained.

EXAMPLE VI

Hexakis(trifluoromethyl)uranium is prepared from $UCl_6$ employing the apparatus described above with the Vycor container being located in the position shown in the FIGURE. Five grams of $UCl_6$ is placed in the Vycor container and the reaction chamber is evacuated to $10^{-3}$ torr. Hexafluoroethane then is admitted to the reactor at a flow rate of 15 cc/min to maintain a 0.5 to 1 mm pressure during pumping. The plasma is initiated at 10 megahertz and 20 watts with a radio frequency generator. After ten hours the product is removed along with fluorocarbons from a $-196°$ C trap downstream from the plasma rector. The product is separated from fluorocarbons by trap to trap distillation and purified by using a liquid nitrogen still technique. A very volatile solid is obtained. This compound, $U(CF_3)_6$ exhibits a P-19 and P—$CF_3$ in its mass spectrum.

EXAMPLE VII

Tetrakis(trifluoromethyl)uranium is prepared from $UBr_4$ employing the apparatus described above with the Vycor container being located in the position hown in FIGURE. figure. Five grams of $UBr_4$ is placed in the Vycor container and the reaction chamber is evacuated to $10^{-3}$ torr. Hexafluoroethane then is admitted to the reactor at a flow rate of 15 cc/min to maintain a 0.5 to 1 mm pressure during pumping. The plasma is initiated at 10 megahertz and 20 watts with a radio frequency generator. After ten hours the product is removed along with fluorocarbons from a $-196°$ C trap downstream from the plasma reactor. The product is separated from fluorocarbons by trap to trap distillation and purified by using a liquid nitrogen still technique. A very volatile solid is obtained which exhibits a P-19 and P—(CF$_3$) in its mass spectrum.

EXAMPLE VIII

Tetrakis(trifluoromethyl)platinum is prepared by employing the apparatus described above with the Vycor container being located in the position shown in the FIGURE. Five grams of PtI$_4$ is placed in the Vycor container and the reaction chamber is evacuated to 10$^{-3}$ torr. Hexafluoroethane then is admitted to the reactor at a flow rate of 15 cc/min to maintain a 0.5 to 1 mm pressure during pumping. The plasma is initiated at 10 megahertz and 20 watts with a radio frequency generator. After ten hours the product is removed along with fluorocarbons from a −196° C trap downstream from the plasma reactor. The product is separated from fluorocarbons by trap to trap distillation and purified by using a liquid nitrogen still technique. A very volatile solid is obtained which exhibits a P-19 and P—CF$_3$ in its mass spectrum.

EXAMPLE IX

Al$_2$(CF$_3$)$_6$ is prepared from AlI$_3$ employing the apparatus described above with the Vycor container being located in the position shown in the FIGURE. Five grams of AlI$_3$ is placed in the Vycor container and the reaction chamber is evacuated to 10$^{-3}$ torr. Hexafluoroethane then is admitted to the reactor at a flow rate of 15 cc/min to maintain a 0.5 to 1 mm pressure during pumping. The plasma is initiated at 10 megahertz and 20 watts with a radio frequency generator. After ten hours the product is removed along with fluorocarbons from a −196° C trap downstream from the plasma reactor. The product is separated from fluorocarbons by trap to trap distillation and purified by using a liquid nitrogen still technique. A very volatile compound was obtained which exhibits a P-19 and P—CF$_3$ in its mass spectrum. The F$^{19}$ N.M.R. is a singlet at room temperature which splits into a doublet at −45° C indicating the dimer structure.

EXAMPLE X

This example illustrates that the process of this invention is useful for forming trifluoromethyl-substituted organic compounds from a wide variety of halide-substituted organic compounds. The apparatus described above was employed in each of the runs with the substrate being placed in the Vycor if it lacked substantial vapor pressure as in the FIGURE or it was bled into the tail of the plasma as described previously if it were sufficiently volatile. The starting halide-substituted reactants and products obtained are shown in Table II.

TABLE II

| Starting Material | Product |
|---|---|
| 1-bromoheptane | 1-trifluoromethylheptane |
| bromobenzene | trifluoromethylbenzene |
| bromocyclohexane | trifluoromethylcyclohexane |

In separate runs approximatley 2 grams of the starting material was vaporized into the tail of the plasma generated by a 10 megahertz 20 watt radio frequency generator. The reactor had been evacuated to the 10$^{-3}$ torr and then 15 cc/min hexafluoroethane were admitted to the reaction to maintain a 0.5 to 1 mm pressure during constant pumping. After eight hours the product was recovered from a −196° C trap downstream along with fluorocarbons. The product was separated from the fluorocarbons by trap to trap distillation and purified using a liquid nitrogen cooled gas chromatographic column. The product was characterized by retention time in the gas chromatograph, F$^{19}$ and H$^1$ N.M.R. separately, mass spectrum and infrared spectrum. The yield of each product was over 30% based on hydrocarbon reactant. The carbonhalogen substitution reaction in addition to providing a route to useful trifluoromethyl fluorocarbon raw materials, provides a route to selectively substituted trifluoromethyl substituted drugs, such as 5-trifluoromethyl uracil.

EXAMPLE XI

This example illustrates the preparation of bis(trifluoromethyl)tellurium and the preparation of per(trifluoromethyl)tellurium polymers including the dimer. 5 Grams of TeBr$_4$ was placed in the Vycor container located at the position shown in the FIGURE and the reaction chamber was evacuated to 10$^{-3}$mm. Hexafluoroethane was admitted to the reactor at flow rate of 15 cc/min to maintain a 0.5 to 1 mm pressure during the pumping. The discharge was initiated at 10 megahertz and 20 watts with a radio frequency generator. After eight hours, the products were removed along with fluorocarbons from a −196° C trap downstrem from the plasma reactor. After the most volatile fluorocarbons were removed a yellow polymer consisting of [Te(CF$_3$)$_2$]n units was recovered in 30% yield which exhibited a mass spectrum containing Te(CF$_3$)$_2$+ specimen.

Te(CF$_3$)$_2$ (20% yield) and Te$_2$(CF$_3$)$_2$ (33% yield) were recovered from the volatile fluorocarbons by trap to trap distillation and purified by separation in a liquid nitrogen still. Te(CF$_3$)$_2$ is a yellow-green liquid which distills at −98° C in vacuo and has a mass spectrum containing both a Te(CF$_3$)$_2$ −19 and a Te(CF$_3$)$_2$ −69 peak in addition to the parent peak. The infrared spectrum contains bands at 1175(s), 114(s), 1224(s), 1069(s), 778(m) and 735(s). The F$^{19}$ N.M.R. occurs at −54 ppm from external trifluoroacetic acid with a J$_{125}$ Te—F = 11 Hz.

Te$_2$(CF$_3$)$_2$ is a red-brown liquid which distills at −53° C. The mass spectrum contains a parent and a Te$_2$(CF$_3$)$_2$−69$^+$ peak. The F$^{19}$ N.M.R. occurs at −49.8 ppm from external trifluoroacetic acid, with a coupling constant of J$_{125}$ Te—F = 46.3 Hz. The infrared spectrum contains bands at 1778(m), 1250(s), 1151(s), 1078(s) and 730(m).

EXAMPLE XII

Following the procedure fo Example V, W(CO)$_6$ was substituted as the substrate and it was reacted with the trifluoromethyl radicals generated in the plasma. The products obtained included W(CF$_3$)$_6$ which was identified by the analytical procedure disclosed in Example V.

We claim:
1. A compound selected from the group consisting of bis(trifluoromethyl)tellurium, tetrakis(trifluoromethyl)M, and hexakis(trifluoromethyl)M' wherein M is tin, germanium, uranium and platinum, and M' is tungsten, uranium and aluminium.
2. Tetrakis(trifluoromethyl)tin.
3. Tetrakis(trifluoromethyl)germanium.
4. Hexakis(trifluoromethyl)tungsten.
5. Hexakis(trifluoromethyl)uranaium.
6. Tetrakis(trifluoromethyl)uuranium.
7. Tetrakis(trifluoromethyl)platinum.
8. Hexakis(trifluoromethyl)aluminum.
9. Bis (trifluoromethyl)tellurium.

\* \* \* \* \*